US00RE45839E

(19) United States
(12) Reissued Patent
Dussarrat

(10) Patent Number: US RE45,839 E
(45) **Date of Reissued Patent: *Jan. 12, 2016**

(54) PENTAKIS(DIMETHYLAMINO) DISILANE PRECURSOR COMPRISING COMPOUND AND METHOD FOR THE PREPARATION THEREOF

(71) Applicant: L'Air Liquide, société anonyme pour l'Etude et l'Exploitation des procédés Georges Claude, Paris (FR)

(72) Inventor: Christian Dussarrat, Tokyo (JP)

(73) Assignee: L'AIR LIQUIDE, SOCIETE ANONYME POUR L'ETUDE ET L'EXPLOITATION DES PROCEDES GEORGES CLAUDE, Paris (FR)

( * ) Notice: This patent is subject to a terminal disclaimer.

(21) Appl. No.: 14/248,894

(22) Filed: Apr. 9, 2014

Related U.S. Patent Documents

Reissue of:
(64) Patent No.: 8,153,832
Issued: Apr. 10, 2012
Appl. No.: 12/295,902
PCT Filed: Apr. 3, 2006
PCT No.: PCT/EP2006/061283
§ 371 (c)(1),
(2) Date: Aug. 5, 2009
PCT Pub. No.: WO2007/112779
PCT Pub. Date: Oct. 11, 2007

(51) Int. Cl.
*C07F 7/10* (2006.01)
*C07F 7/12* (2006.01)

(52) U.S. Cl.
CPC .... *C07F 7/10* (2013.01); *C07F 7/12* (2013.01)

(58) Field of Classification Search
CPC ..... C07F 7/10
USPC ..... 556/410
See application file for complete search history.

(56) References Cited

U.S. PATENT DOCUMENTS 8,377,511 B2 * 2/2013 Dussarrat ..... 427/255.29

FOREIGN PATENT DOCUMENTS

| | | |
|---|---|---|
| WO | WO 2004 044958 | 5/2004 |
| WO | WO 2005 045899 | 5/2005 |
| WO | WO 2005/045899 A2 * | 5/2005 |

OTHER PUBLICATIONS

English translation of Chinese Office Action issued Jan. 20, 2011 for corresponding CN 200680054467.8.
International Search Report for PCT/EP2006/0612183, Aug. 10, 2008.
Wan, Y. et al. "Synthesis of (dialylamino)disilanes." Inorganic Chemistry, 32(3), 341-4, 1993.

* cited by examiner

*Primary Examiner* — Evelyn Huang
(74) *Attorney, Agent, or Firm* — Norton Rose Fulbright US LLP

(57) ABSTRACT

Pentakis(dimethylamino) disilane with general formula (1): Si2(NMe2)5Y, where Y is selected from the group comprising H, Cl or an amino group its preparation method and its use to manufacture gate dielectric films or etch-stop dielectric films of SiN or SiON.

5 Claims, 1 Drawing Sheet

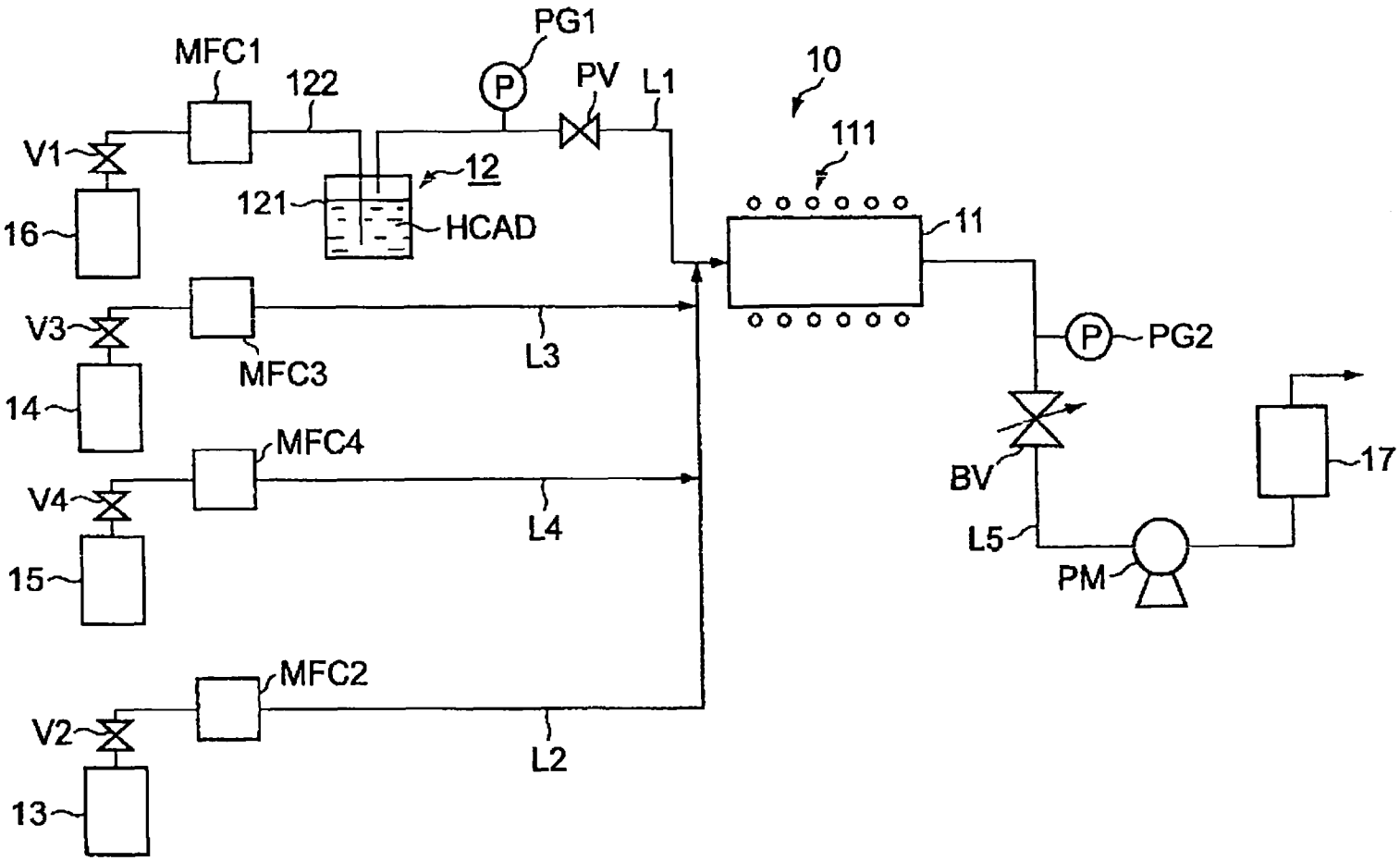
10
111
11
17
PG2
PM
BV
L5
L1
PV
PG1
12
HCAD
121
122
MFC1
MFC3
MFC4
MFC2
L3
L4
L2
V1
V3
V4
V2
16
14
15
13

PENTAKIS(DIMETHYLAMINO) DISILANE PRECURSOR COMPRISING COMPOUND AND METHOD FOR THE PREPARATION THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a 371 of International PCT Application PCT/EP2006/061283, filed Apr. 3, 2006.

This invention relates to disilane compounds and to a method for their preparation. More particularly, this invention relates to pentakis(dimethylamino) disilane $Si_2(NMe_2)_5Y$, with Y being selected from the group comprising Cl, H and an amino group NHR, and to a method for the preparation thereof.

BACKGROUND OF THE INVENTION

Silane compounds such as monosilane and disilane are used in a variety of applications. In the field of semiconductors, silane compounds are frequently used as starting materials for the production by chemical vapor deposition (CVD) of silicon-based dielectric films of, e.g., silicon nitride, silicon oxide, or silicon oxynitride. More specifically, silane compounds can produce silicon nitride by reaction with a nitrogen-containing reaction gas such as ammonia, silicon oxide by reaction with an oxygen-containing gas such as oxygen, and silicon oxynitride by reaction with a nitrogen-containing gas and an oxygen-containing gas.

At present the standard method for producing silicon nitride films by CVD involves inducing a reaction between ammonia gas and dichlorosilane (=the silane compound); however, ammonium chloride is produced as a by-product by this reaction. Ammonium chloride is a white solid and as such accumulates in and clogs the exhaust lines of the CVD reaction apparatus. A CVD method is therefore required in which the starting material is a chlorine-free silane compound. It is also desirable during the production of silicon nitride, etc., by CVD technology to obtain good film-deposition rates at low temperatures (at or below 600° C.).

Tetrakis(dimethylamino) silane and tetrakis(diethylamino) silane may be used as chlorine-free silane compounds, but these aminosilane compounds suffer from being usually of low quality (high amount of impurities) and from providing slow film-deposition rates at low temperatures.

The chlorine-free alkylaminodisilanes are also known. These alkylaminodisilanes are solid at ambient temperatures. For example, hexakis(dimethylamino) disilane is reported to undergo sublimation at 230° C. under reduced pressure. Compounds that are solids at ambient temperature have poor handling characteristics.

SUMMARY OF THE INVENTION

An object of this invention, therefore, is to provide novel silane compounds, that provide excellent film depositing characteristics at low temperatures in the case of silicon nitride and silicon carbonitride films and that also have excellent handling characteristics.

Another object of this invention is to provide a method for preparing these novel silane compounds.

The first aspect of this invention provides pentakis(dimethylamino) silane precursors comprising compounds, said precursors having the formula:

$$Si_2(NMe_2)_5Y \quad (I)$$

wherein Y is selected from the group comprising Cl, H and an amino group. Preferably the amino group is $NH(C_nH_{2n+1})$ with $0 \le n \le 5$.

In accordance with one preferred aspect of the invention, the precursor containing compound shall comprise less than 5% vol of $Si_2(NMe_2)_6$ More preferably the precursor according to the invention is pentakis(dimethylamino) chloro disilane.

The second aspect of this invention provides a method for the preparation of pentakis(dimethylamino) disilane precursor comprising compounds said precursor having the formula (I)

$$Si_2(NMe_2)_5Y \quad (I)$$

wherein each Y represents H, Cl or an amino ligand (NHR) with R being $(C_nH_{2n+1})$ with $0 \le n \le 5$.

said method being characterized in a first step by reacting hexachlorodisilane in an organic solvent with at least, preferably, 5-fold moles of dimethylamine $(CH_3)_2NH$ to generate a $Si_2(NMe_2)_5Cl$ comprising compound.

According to this first step, the pentakis(dimethylamino) chloro disilane comprising compound of the invention is produced;

Starting from there, other compounds may be manufactured such as $Si_2(NMe_2)_5H$ or $Si_2(NMe_2)_5[NH(C_nH_{2n+1})]$ with $0 \le n \le 5$.

In order to do so there is provided a second step according to the process of the invention wherein the remaining chlorine may be substituted to form the pentakis(dimethylamino) disilane $Si_2(NMe_2)_5Y$, for instance by H to form $Si_2(NMe_2)_5H$ by using a reductant such as $LiAlH_4$ and $NaBH_4$, or alternatively by an amino group such as $NH_2$, NHMe, NHEt or $NHR^1R^2$ by using $Li(NR^1R^2)$, with $R^1R^2$ being selected from the group comprising $(C_nH_{2n+1})$ with $0 \le n \le 5$.

DETAILED DESCRIPTION OF THE INVENTION

Pentakis(dimethylamino) chloro disilane $Si_2(NMe_2)_5Cl$ can be synthesized by reacting hexachlorodisilane ($Cl_3Si$—$SiCl_3$) in an organic solvent with at least 5-fold moles of dimethylamine $(CH_3)_2NH$.

However, the use of an excess of dimethylamine (beyond 5-fold) over hexachlorodisilane is preferred. More particularly, the use of a hexachlorodisilane: dimethylamine molar ratio of 1:10 to 1:20 is preferred. The use of at least 10 moles dimethylamine per 1 mole hexachlorodisilane also enables trapping, the hydrogen chloride (6 moles) that is produced as a by-product in the reaction to make dimethylamonium chloride (solid). This dimethylamomium chloride can be easily removed from the reaction mixture by filtration.

Organic solvent may be used as the reaction solvent for reaction of the hexachlorodisilane and dimethylamine. This organic solvent may be tetrahydrofuran, linear chain branched or cyclic hydrocarbons such as pentane, hexane, and octane. However, n-hexane is the preferred solvent.

The reaction between hexachlorodisilane and dimethylamine is preferably run at a temperature from −30° C. to +50° C. In general, this reaction will be run by first bringing the reaction solvent to a temperature in the preferred range of −30° C. to +50° C., adding/dissolving the dimethylamine in the reaction solvent, and then gradually adding the hexachlorodisilane, for example, by dropwise addition. The hexachlorodisilane can be dropped in either pure or dissolved in the same solvent as the reaction solvent. The reaction is subsequently run for 2 to 24 hours while stirring the reaction solvent and holding at the aforementioned temperature. After this period of stirring, the reaction solvent is heated to room temperature (approximately 20° C. to 50° C.) and stirring is preferably continued for at least another 10 hours. The dimethylamomium chloride, a solid by-product, is then removed by filtration and the solvent and residual amine are distilled off in vacuo. The resulting pentakis(dimethylamino) chloro disilane can be subjected to additional purification by fractional distillation.

The resulting pentakis(dimethylamino) chloro disilane can be itself used as a starting material for other attractive materials for silicon carbonitride precursors. One of them is pentakis(dimethylamino) disilane $Si_2(NMe_2)_5H$. It can be formed by reduction of pentakis(dimethylamino) chloro disilane using lithium aluminum hydride or sodium boron hydride.

Pentakis(dimethylamino) monoethylamine disilane $Si_2(NMe_2)_5(NHEt)$ is another molecule of interest. It can be formed by ammonolysis of pentakis(dimethylamino) chloro disilane using monoethylamine. Similar pentakis(dimethylamino) amine disilane $Si_2(NMe_2)_5(NHR)$ where R represents hydrogen or a $C_1$-$C_4$ chain either linear, branched or cyclic, can be manufactured.

Pentakis(dimethylamino) chloro disilane and its derivatives according to this invention contain five dimethylamino-ligands, and are highly reactive and support excellent silicon nitride and silicon carbonitride film deposition rates by CVD at low temperatures (between usually 350-500° C.).

The products according to this invention can therefore, in view of the properties described above, be used in the semiconductor industry as a precursor for the manufacture by CVD of silicon nitride and silicon carbonitride dielectric films e.g. for sidewall spacers or etch stop film. They can also be used to carry out silicon oxinitride and silicon carbo oxynitride films by introducing an oxygen containing gas in the reaction chamber.

It is also preferred to preheat the substrate onto which the film will be deposited at a temperature within the range of the temperature deposition of the film on the substrate, e.g. at least 300° C.

BRIEF DESCRIPTION OF THE DRAWINGS

FIG. 1 contains a block diagram that illustrates a first embodiment of a CVD reaction apparatus that can be used to carry out the invention.

FIG. 1 contains a block diagram that illustrates one example of a CVD reaction apparatus well suited for execution of the inventive method for producing silicon (oxy)nitride films.

The CVD reaction apparatus 10 illustrated in FIG. 1 is provided with a CVD reaction chamber 11, a supply source 12 for the disilane compound (HCAD) according to this invention, a nitrogen-containing gas supply source 13, and a supply source 14 of dilution gas, such as an inert gas, that is introduced as necessary. The CVD reaction apparatus 10 is also provided with an oxygen-containing gas supply source 15 when silicon oxynitride is to be produced. The reaction chamber 11 is surrounded by a heating means 111 for the purpose of heating to the specified CVD reaction temperature (batch processing). A susceptor is heated in the case of single wafer processing.

In the case of the CVD reaction apparatus 10 illustrated in FIG. 1, the HCAD is introduced into the reaction chamber 11 in the gas phase due to the action of a bubbler. The HCAD supply source 12 is provided with a sealed container 121 that is loaded with liquid HCAD compound or solution. An injection conduit 122 is inserted into the sealed container 121 in order to inject carrier gas into the HCAD loaded in the sealed container 121; the carrier gas is injected from the supply source 16 for the carrier gas, e.g., nitrogen, across the valve V1 and mass flow controller MFC1. After its injection into the HCAD, the HCAD-entraining carrier gas passes through the pressure-control valve PV and into the line L1 and is introduced into the reaction chamber 11. A pressure sensor PG1 is connected to the line L1. Although not shown in the figure, at least 1 substrate (typically a semiconductor substrate such as a silicon substrate) is loaded in the reaction chamber 11. From 1 to 250 substrates (chuck- or wafer boat-loaded) can be present.

Nitrogen-containing gas, e.g., ammonia, is introduced from the nitrogen-containing gas supply source 13 across the valve V2 and the mass flow controller MFC2 and into the reaction chamber 11 through the line L2.

Dilution gas, which is introduced as necessary, can be introduced from the dilution gas supply source 14 across the valve V3 and the mass flow controller MFC3 and into the reaction chamber 11 through the line L3 and the line L2.

Oxygen-containing gas, which is introduced during production of silicon oxynitride films, can be introduced from the oxygen-containing gas supply source 15 across the valve V4 and the mass flow controller MFC4 and into the reaction chamber 11 through the line L4 and the line L2.

The outlet from the reaction chamber 11 is connected by the line L5 to a waste gas treatment apparatus 17. This waste gas treatment apparatus 17 functions to remove, for example, by-products and unreacted material, and to—exhaust the gas after abatement from the system. A pressure sensor PG2, a butterfly valve BV, and a pump PM are connected in the line L5. The various gases are introduced into the reaction chamber 11, the pressure within the reaction chamber 11 is monitored by the pressure sensor PG2, and the pressure is brought to its prescribed value by the opening and closing of the butterfly valve BV by the operation of the pump PM.

During operation, the container 121 is heated to, for example, 50° C. to 80° C., and the HCAD feed system, which comprises the line L1, is preferably heated to a temperature higher than the bubbler in order to prevent dew formation by the HCAD.

The invention will now be described in greater details in the following examples:

EXAMPLE 1

The synthesis of $ClSi_2(NMe_2)_5$ has been done from the ammonolysis of hexachlorodisilane and lithium dimethylamide. Hexachlorodisilane (HCD) is used as the starting material so that the Si-Si direct bond remains in the molecule. n-hexane is used as a solvent and cooled at 0° C. A mixture of pentakis(dimethylamino) chloro disilane and hexakis(dimethylamino) disilane is obtained. Lithium dimethylamide is added to form a "lithium dimethylamide solution". HCD is added dropwise in the 0° C. lithium dimethylamide solution. Then the solution is stirred for 2 h at 0° C. then for 15 h at RT. The salt LiCl is then removed from the solution, and the n-hexane removed in vacuo. The resulting $ClSi_2(NMe_2)_5$ and other byproducts are separated by fractional distillation.

The NMR spectra indicates that the samples obtained from this distillation process contain less than 5% vol of $Si_2(NMe_2)_6$.

EXAMPLE 2

The precursor pentakis(dimethylamino) chloro disilane was dissolved in toluene 18.5 weight % to be delivered using a liquid delivery system. This percentage has been found to be optimum in terms of solubility and for an easy delivery to the vaporizer and then to the CVD chamber. The corresponding solution will be described below as "$Si_2(NMe_2)_5Cl$ solution". However, this definition comprises all solutions of $Si_2(NMe_2)_5Cl$ (or other products of the same "family" as explained with 1% to 20% weight of at least one solvent, preferably selected from the group comprising benzene, toluene, etc.

EXAMPLE 3

A typical set-up is described FIG. 1. An inert gas, such as helium, argon, nitrogen or the like having the purity required for semiconductor manufacturing was introduced into the bubbler so that the solution is introduced into the liquid mass flow controller and the vaporizer. The components of the solution are then vaporized at a suitable temperature in order to optimize the delivery. An inert gas, such as helium, argon, nitrogen or the like having the purity required for semi conductor manufacturing is separately introduced into the vaporizer to carry the gaseous components of the solution to the CVD reactor. It can be mixed with an additional reactant such as ammonia.

Helium is considered as the most suitable carrier gas in this application.

EXAMPLE 4

The different reactants are introduced into the CVD chamber as described on FIG. 1.

The feed rates of the different chemicals involved into the process are:

$Si_2(NMe_2)_5Cl$ solution: 0.08 g/min. He: 175 sccm. $NH_3$: 35 sccm

The deposition parameters are:

Vaporizer in which the "solution" is vaporized in gaseous form T: 110° C.

Deposition T: 525° C. CVD reactor pressure: 1.0 Torr. Duration: 20 minutes

The film has been characterized by AES and refractometry.

The corresponding deposition rate is 75 A/min

The film composition is then: $Si_{0,65}N_{0,14}C_{0,21}$

The results obtained in examples 2-4 are summarized on figure FIG. 2. The corresponding apparent activation energy is 14 kcal/mol, less lower than the activation energy of HCDS/$NH_3$ process, known as a process giving nitride and carbonitride films having excellent properties.

EXAMPLE 5

The different reactants are introduced into the CVD chamber as described on FIG. 1.

The feed rates of the different chemicals involved into the process are:

$Si_2(NMe_2)_5Cl$ solution: 0.08 g/min. He: 175 sccm, $NH_3$: 35 sccm

The deposition parameters are:

Vaporizer T: 110° C. Deposition T: 500° C. CVD reactor pressure: 1.0 Torr.

Duration: 30 minutes

The film has been characterized by AES and refractometry.

The corresponding deposition rate is 40 A/min

The film composition is then: $Si_{0,62}N_{0,14}C_{0,23}$

EXAMPLE 6

The different reactants are introduced into the CVD chamber as described on FIG. 1.

The feed rates of the different chemicals involved into the process are:

$Si_2(NMe_2)_5Cl$ solution: 0.08 g/min. He: 175 sccm. $NH_3$: 35 sccm

The deposition parameters are:

Vaporizer T: 110° C. Deposition T: 475° C. CVD reactor pressure: 1.0 Torr.

Duration: 30 minutes

The film has been characterized by AES and refractometry.

The corresponding deposition rate is 19 A/min

The film composition is then: $Si_{0,62}N_{0,15}C_{0,23}$

EXAMPLE 7

The different reactants are introduced into the CVD chamber as described on FIG. 1.

The feed rates of the different chemicals involved into the process are:

$Si_2(NMe_2)_5Cl$ solution: 0.08 g/min. He: 175 sccm. $NH_3$: 35 sccm

The deposition parameters are:

Vaporizer T: 110° C. Deposition T: 450° C. CVD reactor pressure: 1.0 Torr.

Duration: 50 minutes

The film has been characterized by AES and refractometry.

The corresponding deposition rate is 6 A/min

The film composition is then: $Si_{0,56}N_{0,17}C_{0,26}$

EXAMPLE 8

The different reactants are introduced into the CVD chamber as described on FIG. 1.

The feed rates of the different chemicals involved into the process are:

$Si_2(NMe_2)_5Cl$ solution: 0.16 g/min. He: 175 sccm. $NH_3$: 35 sccm

The deposition parameters are:

Vaporizer T: 110° C. Deposition T: 450° C. CVD reactor pressure: 1.0 Torr.

Duration: 50 minutes

The film has been characterized by AES and refractometry.

The corresponding deposition rate is 11.2 A/min, about twice that obtained in the previous example where the feed rate of the precursor was twice lower.

The film composition is then: $Si_{0,62}N_{0,14}C_{0,24}$

EXAMPLE 9

The different reactants are introduced into the CVD chamber as described on FIG. 1.

The feed rates of the different chemicals involved into the process are:

$Si_2(NMe_2)_5Cl$ solution: 0.16 g/min. He: 175 sccm. $NH_3$: 35 sccm

The deposition parameters are:

Vaporizer T: 110° C. Deposition T: 425° C. CVD reactor pressure: 1.0 Torr.

Duration: 80 minutes

The film has been characterized by AES and refractometry.

The corresponding deposition rate is 3 A/min

The film composition is then: $Si_{0,56}$ $N_{0,17}$ $C_{0,26}$

EXAMPLE 10

"Subatmospheric CVD" experiments

The different reactants are introduced into the CVD chamber as described on FIG. 1.

The feed rates of the different chemicals involved into the process are:

$Si_2(NMe_2)_5Cl$ solution: 0.08 g/min. He: 175 sccm. $NH_3$: 35 sccm

The deposition parameters are:

Vaporizer T: 110° C. Deposition T: 400° C. CVD reactor pressure: 100 Torr.

Duration: 80 minutes

The film has been characterized by AES and refractometry.

The corresponding deposition rate is 28 A/min

The film composition is then: $S_{0,41}$ $N_{0,51}$ $C_{0,07}$

EXAMPLE 11

The different reactants are introduced into the CVD chamber as described on FIG. 1.

The feed rates of the different chemicals involved into the process are:

$Si_2(NMe_2)_5Cl$ solution: 0.08 g/min. He: 175 sccm. $NH_3$: 35 sccm

The deposition parameters are:

Vaporizer T: 110° C. Deposition T: 375° C. CVD reactor pressure: 100 Torr.

Duration: 80 minutes

The film has been characterized by AES and refractometry.

The corresponding deposition rate is 20 A/min

The film composition is then: $Si_{0,41}$ $N_{0,51}$ $C_{0,07}$

EXAMPLE 12

The different reactants are introduced into the CVD chamber as described on FIG. 1.

The feed rates of the different chemicals involved into the process are:

$Si_2(NMe_2)_5Cl$ solution: 0.08 g/min. He: 175 sccm. $NH_3$: 35 sccm

The deposition parameters are: Vaporizer T: 110° C. Deposition T: 350° C. CVD reactor pressure: 100 Torr.

Duration: 80 minutes

The film has been characterized by AES and refractometry.

The corresponding deposition rate is 15 A/min

The film composition is then: $Si_{0,40}$ $N_{0,51}$ $C_{0,08}$

The apparent activation energy of the process according to examples 10 to 12 is 14 kcal/mol, very close to the DCS/$NH_3$ process, known as a process giving nitride or carbonitride films having excellent properties.

COMPARATIVE EXAMPLE 13

This example (Table 1) summarizes the comparison between a SiN film obtained from a prior art $Si_2(NHEt)_6$ precursor and a SiN film obtained from the $Si_2(NMe)_5Cl$ precursor according to the invention. The etch rate of the compound according to the invention is 400 times less than the etch rate of the prior art layer from $Si_2(NHEt)_6$ which makes it particularly attractive to make SiN layers for etch-stop purpose.

TABLE 1

| | $Si_2(NMe)_5Cl$ | $Si_2(NHEt)_6$ |
|---|---|---|
| Precursor flow rate (ccm) | 0.05 | 0.05 |
| NH3 (sccm) | 35 | 35 |
| Deposition temperature (° C.) | 450 | 450 |
| Operating pressure (Torr) | 1 | 1 |
| Deposition rate (A/min) | 6 | 7 |
| Etch rate in 5% HF (A/min) | 5 | 2000 |

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A pentakis(dimethylamino) disilane precursor having the formula:

$$Si_2(NMe_2)_5Y \quad (I)$$

wherein Y is *H or* the amino group $NH(C_nH_{2n+1})$ with $0 \leq n \leq 5$.

2. The precursor of claim 1, wherein said precursor comprises less than 5% vol. of $Si_2(NMe_2)_5$.

3. A method for the preparation of pentakis(dimethylamino) disilanes precursor having the formula (I)

$$Si_2(NMe_2)_5Y \quad (I)$$

wherein each Y represents an amino ligand (NHR) with R being $(C_nH_{2n+1})$ with $0 \leq n \leq 5$, said method being characterized in a first step, by reacting hexachlorodisilane in an organic solvent with, at least, preferably, 5-fold moles of dimethylamine $(CH_3)_2NH$ to generate a $Si_2(NMe_2)_5Cl$ comprising compound; and a second step wherein the remaining chlorine of the $Si_2(NMe_2)_5Cl$ comprising compound is substituted by an amino group such as $NHR^1R^2$ by using $Li(NR^1R^2)$, or $NHR^1R^2$, with $R^1R^2$ being selected from the group comprising $(C_nH_{2n+1})$ with $0 \leq n \leq 5$ to form $Si_2(NMe_2)_5[NH(C_nH_{2n+1})]$ with $0 \leq n \leq 5$.

4. The method for preparation of claim 3, wherein the reaction is run at a temperature from −30° C. to 50° C.

5. The method for preparation of claim 3, wherein the organic solvent is n-hexane.

* * * * *